US005780850A

United States Patent [19]

DeLaune et al.

[11] Patent Number: 5,780,850
[45] Date of Patent: Jul. 14, 1998

[54] API ESTIMATE USING MULTIPLE FLUORESCENCE MEASUREMENTS

[75] Inventors: Patrick Lee DeLaune; Kerry Kennedy Spilker, both of Houston; Alan Cameron Wright, Bellaire, all of Tex.

[73] Assignee: Texaco Inc., White Plains, N.Y.

[21] Appl. No.: 664,485

[22] Filed: Jun. 17, 1996

Related U.S. Application Data

[60] Provisional application No. 60/012,830 Mar. 5, 1996.

[51] Int. Cl.$^6$ .................................................. G01V 5/00
[52] U.S. Cl. ............................................. 250/255; 250/301
[58] Field of Search .................................. 250/255, 301, 250/458.1; 364/498, 499

[56] References Cited

U.S. PATENT DOCUMENTS

| | | | |
|---|---|---|---|
| 4,814,614 | 3/1989 | Tsui | 250/255 |
| 4,977,319 | 12/1990 | Supernaw | 250/301 |
| 4,990,773 | 2/1991 | Supernaw et al. | 250/255 |
| 5,049,738 | 9/1991 | Gergely et al. | 250/255 |

*Primary Examiner*—Bruce Anderson
*Attorney, Agent, or Firm*—Henry H. Gibson; William J. Beard

[57] ABSTRACT

A method for evaluating the API gravity of a sample of underground formation includes steps of:

Solvating a known volume of an underground formation sample in a known volume of a solvent which will solvate hydrocarbons;

Quantitatively measuring with a changeable filter portable fluorometer the emission fluorescence of the solvated sample at a fixed excitation wavelength with measurements of emission intensities at two points;

characterizing the oil by the ratio of two emission intensities obtained at a fixed excitation wavelength;

determining the yield;

applying regression analysis to a data base of oils to obtain an equation which results in an algorithm value; and interpreting the value of the algorithm to give a value for API gravity and estimate in-situ oil concentration.

12 Claims, 4 Drawing Sheets

API ESTIMATE USING MULTIPLE FLUORESCENCE MEASUREMENTS

CROSS-REFERENCE

This application is a continuation-in-part of Provisional Application 60/012,830, filed Mar. 5, 1996.

FIELD OF THE INVENTION

The invention is related to techniques for evaluating the hydrocarbon content and composition of an underground formation. More particularly, the invention relates to fluorescence measurements and to their use in characterizing oils/oil extracts to determine similarities of oils from different sources. Still more particularly this invention relates to a method of using a portable fluorometer in the field to provide a reliable value for the API gravity range ($\pm 5°$) of in-situ liquid hydrocarbon.

BACKGROUND OF THE INVENTION

Fluorescence has been used for decades as a logging technique for detecting oil in drill cuttings. For much of that time the method used to determine the presence of oil in drill cuttings was crude, wherein an operator exposed the cuttings sample to a broad spectrum ultraviolet light in order to see fluorescence which indicated the presence of oil.

Ultra-violet fluorescence spectroscopy has long been used as a means for detecting aromatic hydrocarbons. Important applications for this technology include the measurement of petroleum hydrocarbons in samples such as drill cuttings, cores, and soil samples by fluorescence examination of solvent extracts of these solids.

Molecular fluorescence is discussed in general in *Principles of Instrumental Analysis*, by Skoog, Douglas, Sanders College Publishing, Philadelphia (3rd ed. 1985), pp 225–240. The discussion in this reference indicates that the greatest fluorescence behavior occurs with compounds containing aromatic functional groups and includes a table which gives the UV fluorescence wavelengths associated with numerous benzene derivatives in ethanol solution. Also several analytical profiles of hydrocarbons are disclosed wherein fluorescence intensity is plotted over multiple excitation and emission wavelengths.

Fluorescence spectrophotometry is also used for oil prospecting via remote sensing or near surface sampling methods. In U.S.G.S. Open-File Report 84–385, 34 pp (1984), in an article by M. E. Henry and T. S. Donovan entitled "Luminescence Properties and Chemical Geochemical Prospecting", there is a discussion of the technology for this use. The use of fluorescence techniques for geochemical prospecting is discussed in an article by C. F. Hebert entitled, "Geochemical Prospecting for Oil and Gas Using Hydrocarbon Fluorescence Techniques", 3RD Southern Methodist Univ. Symp.—Unconventional Methods in Exploration for Petroleum and Natural Gas, Processing, (1984) pp. 40–58.

The emission fluorescence of crude oil samples has been studied and recorded over various wavelengths, including ultraviolet wavelengths below 400 nm. There have been "fingerprint" studies at, for example, Bartlesville Energy Technology Center, where the emission fluorescence of various types of crude oils has been recorded at different excitation wavelengths. Research of this type at the Department of Energy was related to earlier work by the Bureau of Mines to try to identify crude oil by emission fluorescence for the purpose of pollution control. See Chisholm, B. R., Eldering, H. G., Giering, L. P., and Horning, A. W. Total Luminescence Contour spectra of six topped crude oils, BETC/RI-76/15, a paper prepared for ERDA for the Bartlesville Energy Research Center in Bartlesville, Okla., Nov. 1976; and Brownrigg, J. T., and Hornig, A. W., Low Temperature Total Luminescence Contour Spectra of Six Topped Crude Oils and Their Vacuum Distillate and Residuum Fractions, BETC/RI -78/13, a paper prepared for DOE for the Bartlesville Energy Technology Center, Bartlesville, Okla., Jul. 1978.

Several patents in recent years disclose the use of fluorescence measurement in methods to test for the presence of hydrocarbons or to determine concentration or producibility.

U.S. Pat. No. 4,609,821 discloses a process to test for the presence of hydrocarbons within drill cuttings. This process is applicable only to oil base mud drill cuttings. The cuttings are excited with a wide range of UV wavelengths and the emitted radiation is recorded over a wide range of wavelengths to produce an analytical chemical profile. This profile of intensity over multiple wavelengths of excitation and emission radiation is compared with previous profiles to determine the presence of hydrocarbons not associated with the oil mud base.

In U.S. Pat. No. 4,977,319, incorporated by reference herein in its entirety, there is disclosed a method of determining the presence and concentration of hydrocarbons in a formation. The method involves the steps of solvating a sample in a known volume of solvent, measuring the emission fluorescence of the excited sample below about 400 nm, and comparing the emission fluorescence to previous correlations drawn between known hydrocarbon contents of samples and the emission fluorescence of the known samples in the solvent.

The method of U.S. Pat. No. 4,990,773, incorporated by reference herein in its entirety, comprises determining the producibility of any hydrocarbons present in a formation by employing two solvents, one of which will solvate all petroleum fractions, including asphaltenes, and a second which will solvate most crude fractions without substantially solvating asphaltenes. An indication of producibility or viscosity can be obtained by comparing the ratio of the emission fluorescence of the two solvated samples with previous correlations.

One property of oil or oil samples which is a valuable tool to technicians is the API gravity of oil. Any information regarding oil gravity is extremely valuable in the decision making and planning required during the development of an oil production prospect, however it is generally not possible to obtain an accurate determination of the API gravity of oil in a production prospect in situ or in the field.

The viscosity and volatility of a crude oil may vary widely with variations in API gravity particularly with respect to gravities above about 50 degrees. For example, in a typical heavy oil prospect, the change in viscosity which accompanies a change of from 11 to 12 degrees in API gravity is approximately 62 centipoises. However, the change in viscosity as the gravity changes from 18 to 19 degrees API is only approximately 3 centipoise. It is important to determine the oil gravity as precisely as possible and as early as possible in the pre-development economic studies of an oil production prospect.

Presently no methods are available for accurate or reliable estimates of in-situ API gravity in the field. The most closely related methods available include:

(a) direct measurements on oil samples recovered from production tests obtained by formation fluid-sampling logging devices or the like;

(b) measurements of the refractive index (RI) of oil retorted from cores or samples of the reservoir formation.

In the latter method, a calibration curve is prepared by retorting oils which have known gravities and similar chemical compositions and measuring the refraction indexes of the liquids condensed from the retorting. The gravity of the oil being tested is then determined by measuring the refractive index of its distillate and assuming that its gravity equals that of an oil of known gravity from which a distillate of similar refractive index is obtained.

Patents in the art relating to the determination of API gravity include, for example, U.S. Pat. Nos. 3,753,654; 3,953,171; 4,153,415; and 4,248,599. Generally the methods available have numerous disadvantages. Although direct measurements are, of course, the most accurate, they are also the most expensive and time consuming or require a relatively large sample. Numerous of the lighter or more volatile components of a crude oil may be cracked or depolymerized during a retorting operation in which the vapors are condensed to a liquid. Because of this a property such as refractive index of the distillate may vary from chemical composition and reactivity factors that are not related to the API gravity of the oil.

It would be extremely advantageous in the art if it were possible to accurately estimate the API gravity of in situ oil. Reliable data would be a valuable planning tool during the development of an oil production prospect.

SUMMARY OF THE INVENTION

In accordance with the foregoing the invention comprises a method of evaluating a sample of underground formation to determine the API gravity of any hydrocarbons present in the formation which comprises:

- solvating a known volume of an underground formation sample in a known volume of a solvent which will solvate hydrocarbons;
- quantitatively measuring with a changeable filter portable fluorometer the emission fluorescence of the solvated sample at a fixed excitation wavelength and measuring emission intensity at two points;
- characterizing the oil by the ratio of the two emission intensities obtained at a field excitation wavelength;
- determining the yield;
- applying regression analysis to a data base of oils to obtain an equation which results in an algorithm value; and
- interpreting the value of the algorithm to give a value for API gravity and concentration.

DESCRIPTION OF THE INVENTION

Figure 1:
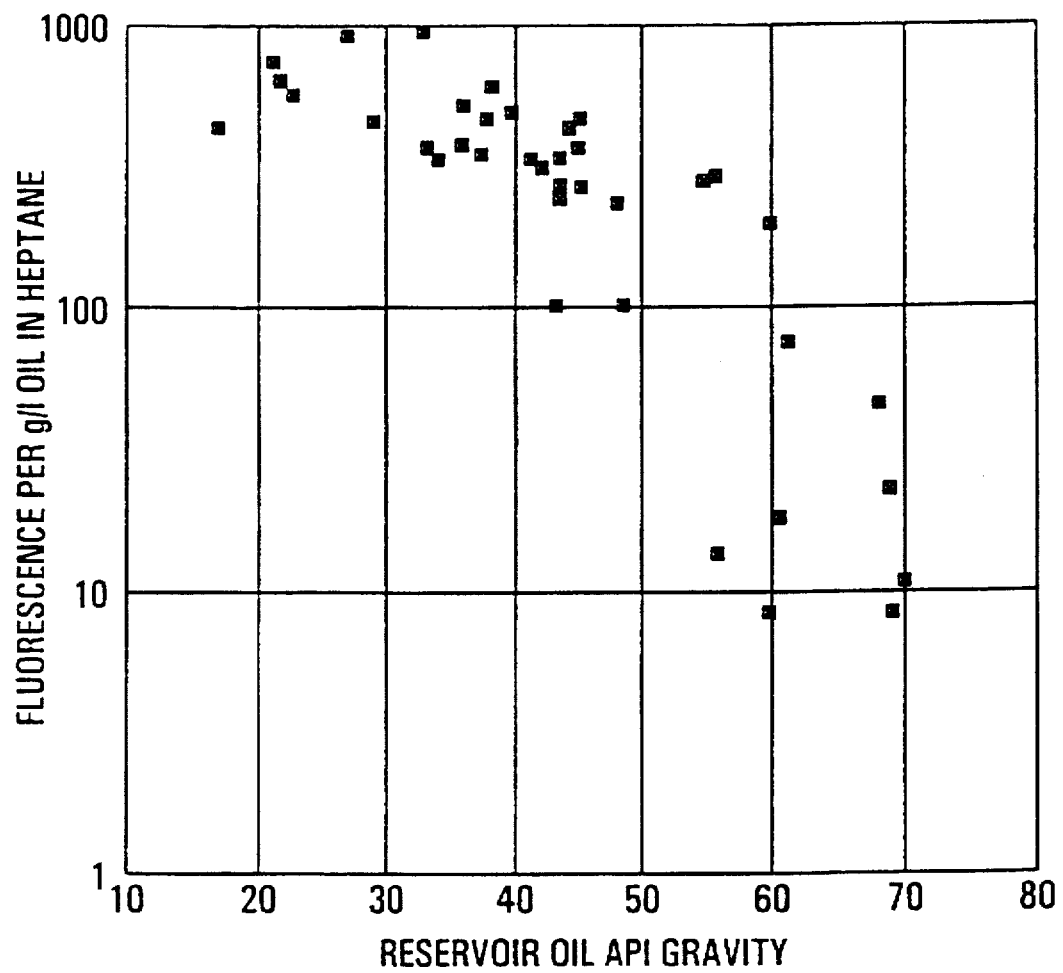
FIG. 1 is a graph which plots the variation in relative fluorescence per weight oil with petroleum oil of type 254 nm Hg line excitation and 320 nm emission using a 20 nm BW filter.

In accordance with the foregoing we have found in the instant invention that for naturally occurring petroleum oils, systematic variations in emission spectra features can be related to fluorescence yield. In this invention portable fluorometers are used to characterize oil by the ratio of two intensities of differing emission wavelengths obtained at fixed excitation (for example by use of the 254 nm mercury line).

As noted, fluorescence is a phenomena wherein certain compounds, containing molecular arrangements generally referred to as chromophores, emit fluorescent radiation when excited by incoming light of certain wavelengths. The chromophores contained in compounds such as the asphaltenic, aromatic and resin fractions of crude, fluoresce in the UV and visible portion of the electromagnetic spectrum when bombarded with radiation of the proper excitation wavelength.

Total scanning (multiple excitation/emission wavelengths) fluorescence (TSF) measurements are used to further characterize oils/oil extracts and determine similarities of oils from different sources. TSF requires a relatively large, computer controlled, permanently installed instrument in a laboratory environment.

In total scanning fluorescence or 3-D fluorescence a sample is excited over a range of discrete wavelengths and the emitted radiation is recorded at various wavelengths (EM) for each sample. Total scanning fluorescence has indicated that the optimum excitation and emission wavelengths for most crude oils fall below 400 nanometers. This is a region undetectable to the human eye. The optimum excitation wavelength for most crude oils is in the region of about 250 to 310 nanometers. The predominant portion of emitted radiation falls in the nonvisible ultraviolet region of about 300 to about 400 nanometers.

Single point (fixed excitation/emission wavelength) fluorescence measurements are used to determine the approximate quantity of oil in formation samples (QFT™). QFT™ is the tradename for Quantitative Fluorescence Technique, a method for detecting oil in formations which was developed and patented by Texaco Inc. (U.S. Pat. No. 4,977,319). QFT™ can be accomplished with a relatively small, portable fluorometer, while TSF requires a relatively large, fixed instrument in a laboratory environment.

By using a scale of fluorescence intensity and instrumentally measuring the fluorescence of a formation sample from cores or drill cuttings a number proportional to the hydrocarbon content of the sample can be derived, as discussed in U.S. Pat. No. 4,977,319, supra.

The primary (most intense) peak for crude oils generally occurs in the spectral region between 300 nm and 360 nm. The position of the maximum fluorescence peak is dependent on the predominant fluorescing species (aromatics) found in the crude oil mixture.

The two to four-ring aromatics and their derivatives have considerable overlap in the 320 nm to 380 nm spectral range. Most of the heavier polyaromatics consisting of five to six rings emit fluorescence to 400 nm and extend into the visible range (410 nm to 800 nm).

As indicated direct measurement on oil samples from production tests by logging devices, has certain limitations. This method is limited by a high degree of variation in fluorescence yield for naturally occurring oils. And, measurement of the refractive index of oil retorted from core samples does not lend itself to use in the field. Furthermore, when developing a new prospect, samples of similar oils may not be available for comparison.

In the present invention it is found that for naturally occurring petroleum oils, systematic variations in emission spectra features can be related to fluorescence yield. A reliable value for API gravity can be ascertained by solvating a known volume of an underground formation sample in a known volume of a solvent which will solvate hydrocarbons, quantitatively measuring with a changeable filter portable fluorometer the emission fluorescence of the solvated sample at two emission intensity points below an excitation wavelength of about 400 nm.

- characterizing the oil by the ratio of two emission intensities obtained at a fixed excitation wavelength;
- determining the yield;
- applying regression analysis to a data base of oils to obtain an equation which results in an algorithm value; and
- interpreting the value of the algorithm to give a value for API gravity and concentration.

Where the sample is oil, rather than a sample such as a side wall sample or drill cuttings, the solvent serves as a diluent.

A wide variety of solvents capable of solvating hydrocarbons may be used in the invention. One suitable group of solvents is low molecular weight aliphatic hydrocarbons having more than four carbon atoms such as pentane, hexane, heptane, and higher. Chlorinated hydrocarbons such as methylene chloride, chloroform, carbon tetrachloride, trichloroethane, and others are also effective, however strong solvents may lessen the accuracy of the invention method due to their ability to dissolve other sample constituents than hydrocarbons. Aromatic solvents are generally not preferred because of their inherent fluorescence.

Another group of solvents which is very useful has been identified and described in copending U.S. Ser. No. 60/012, 830, filed Mar. 5, 1996. This includes oxygenated hydrocarbon solvents possessing hydrophilic and hydrophobic properties. Examples include, but are not limited to, methanol, ethanol, 1-propanol, 2-propanol (isopropanol), 2-methyl-2-propanol, and allyl alcohol. In particular, 2-propanol is capable of breaking through the water barrier while, at the same time, solvating the aromatic portion without extracting asphaltenes and other heavy fractions.

FIG. 1 shows a graph of relative intensities per gm/l oil versus API gravity for a series of reservoir oils diluted in heptane solvent. These values were obtained using 254 nm mercury line excitation and measuring the fluorescence at 320 nm with a 20 nm band-pass interference filter at 90 degrees to the excitation beam. Sample dilutions were adjusted such that absorption effects were less than about 5% relative. The general trend of decreasing fluorescence with increasing API gravity reflects the fact that oils tend to lose aromatic content as they mature. The 100-fold variation in intensity per wt. oil for this fixed point measurement requires that a reference oil similar to the sample oil be available for calibration purposes if absolute oil quantities are desired. In many cases however, the type as well as the amount of oil are unknown so that only relative oil amounts can be determined for those samples judged to contain the same oil type.

Figure 2:
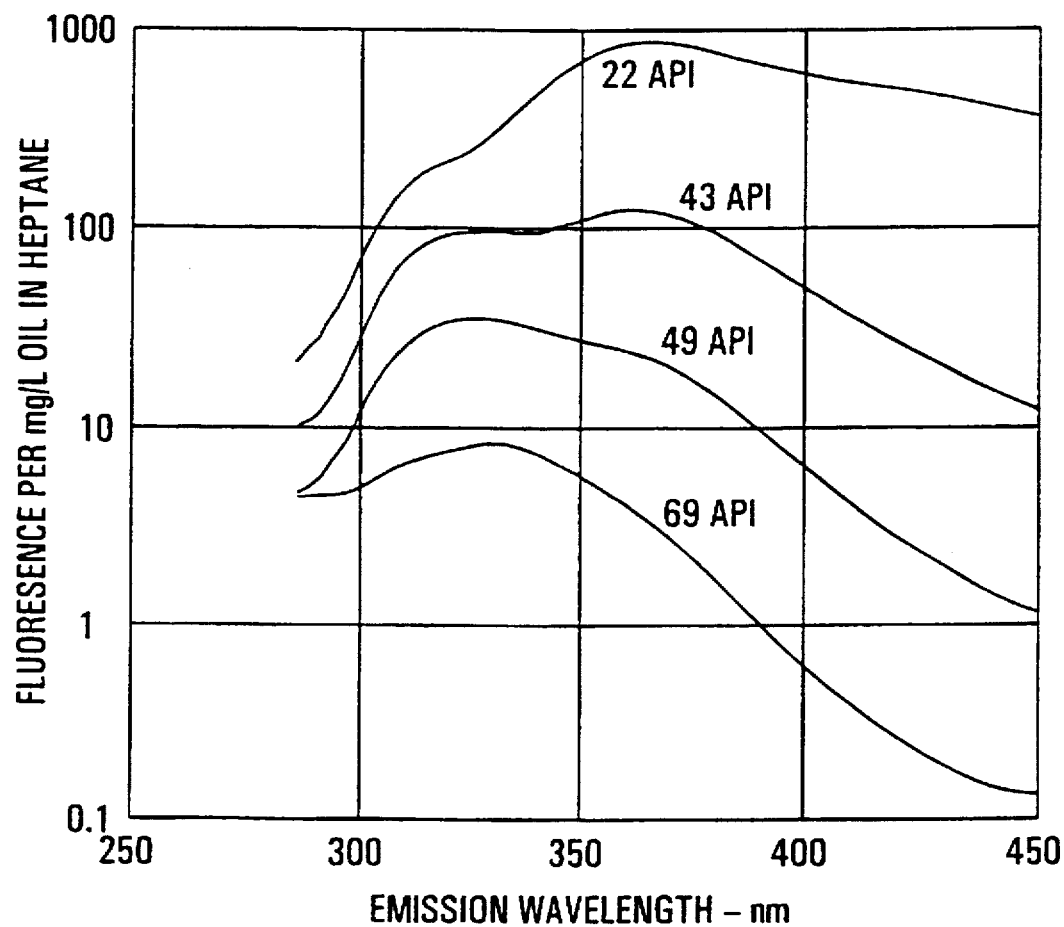
FIG. 2 is a plot of fluorescence per mg/l oil in heptane versus emission wavelength (nm) and shows the typical variation in emission spectra with petroleum oil maturity 254 excitation, 6.25% resolution emission band width.

FIG. 2 presents 254 nm excitation emission spectra for four of the oils in FIG. 1 which have widely differing yields. These scans were obtained from dilute heptane solutions with a grating spectrophotometer using 4 nm slit widths. The spectra have been artificially broadened to mimic the effect of using 6.25% resolution interference filters to demonstrate that high resolution is not required to detect spectral variations of interest. In general, as oils mature (increase in API gravity), fluorescence yield decreases at all wavelengths but the percentage decrease is largest at the longer wavelengths. In compositional terms, this phenomena arises from preferential loss of the larger aromatic structures relative to the smaller.

Because each oil has a unique, highly complex composition based on its detailed genesis, correlations of oil properties with specific spectral features are not perfect. Nonetheless estimation of some properties, fluorescent yield and API gravity in particular, can usefully be performed by characterizing the oil by the ratio of two intensities of differing emission wavelengths obtained at a fixed excitation (for example, by use of the 254 nm mercury line).

For the determination of yield, the ratio of emission intensities at about 290 and 365 nm gives close to optimum correlation. For the purpose of illustration, a yield Y equal to the intensity average divided by the oil concentration will be used:

$$Y=0.5 \ [EM1+EM2] \ / \ (mg/l \ Oil) \qquad (1)$$

Where

EM1=emission at 290 nm for 254 nm excitation

EM2=emission at 365 nm for 254 nm excitation

Application of regression analysis to a data base of 38 oils of widely differing types gives the equation:

$$ln(Y)=0.9494 +0.6575/( R+0.11) \qquad (2)$$

Where

R=EM1/EM2=emission intensity ratio and std dev= 0.3223, r-squared=0.961.

Figure 3:
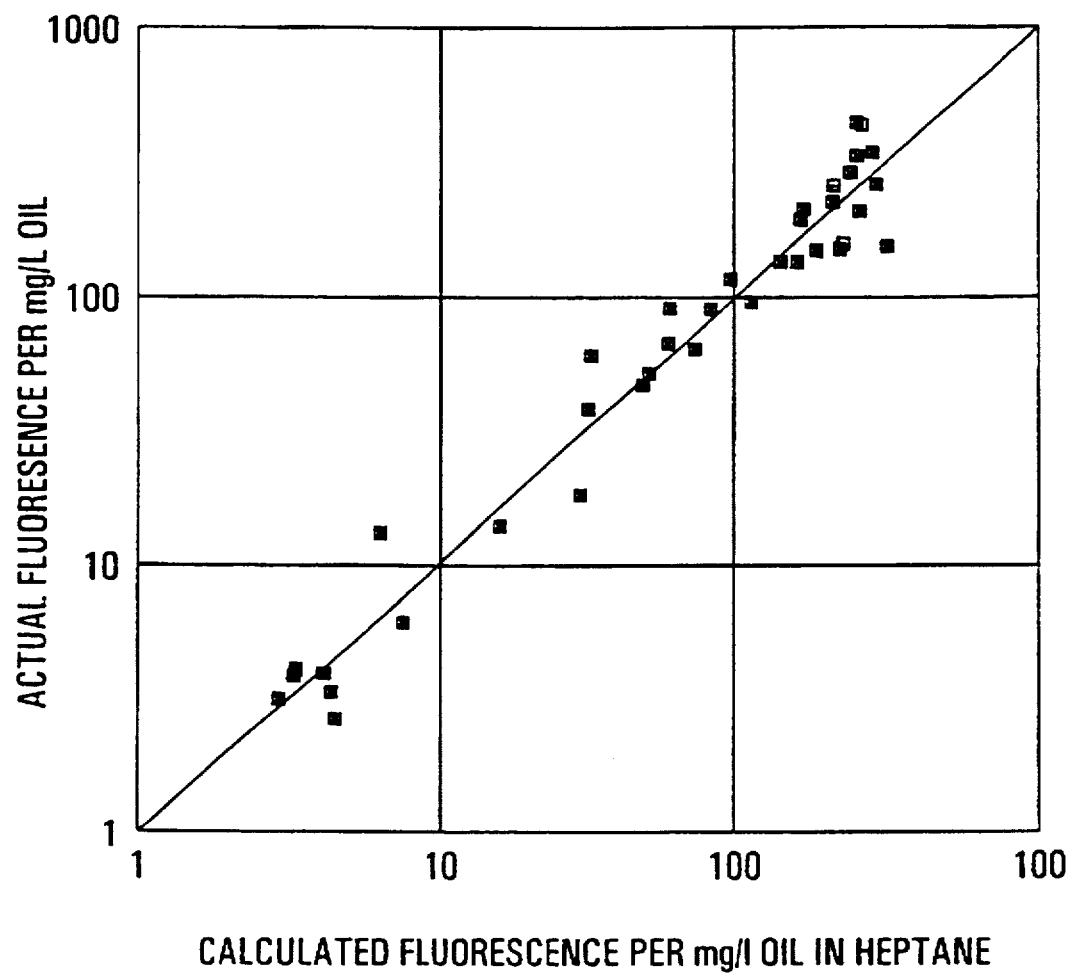
FIG. 3 is a plot of actual fluorescence per mg/l oil versus calculated fluorescence per mg/l oil in heptane, and specifically shows actual versus caluculated fluorescence per wt. oil using emission intensities at 290 nm and 365 nm (6.25% resolution) and 254 nm excitation.

In FIG. 3 are plotted calculated versus actual yields for the oils included in the analyses. The standard deviation obtained indicates that, with 95% confidence, the actual yield can be calculated for equation (2) to within a factor of 1.9. While this uncertainty precludes use of the method for precise oil quantitation, it is substantially smaller than the 100-fold uncertainty seen for the single point technique.

Regression of the same intensity ratio against API gravity gives the equation:

$$API=66.05-3.170/(R+0.06) \qquad (3)$$

with std. dev−7.1 deg API, r-squared−0.753

Figure 4:
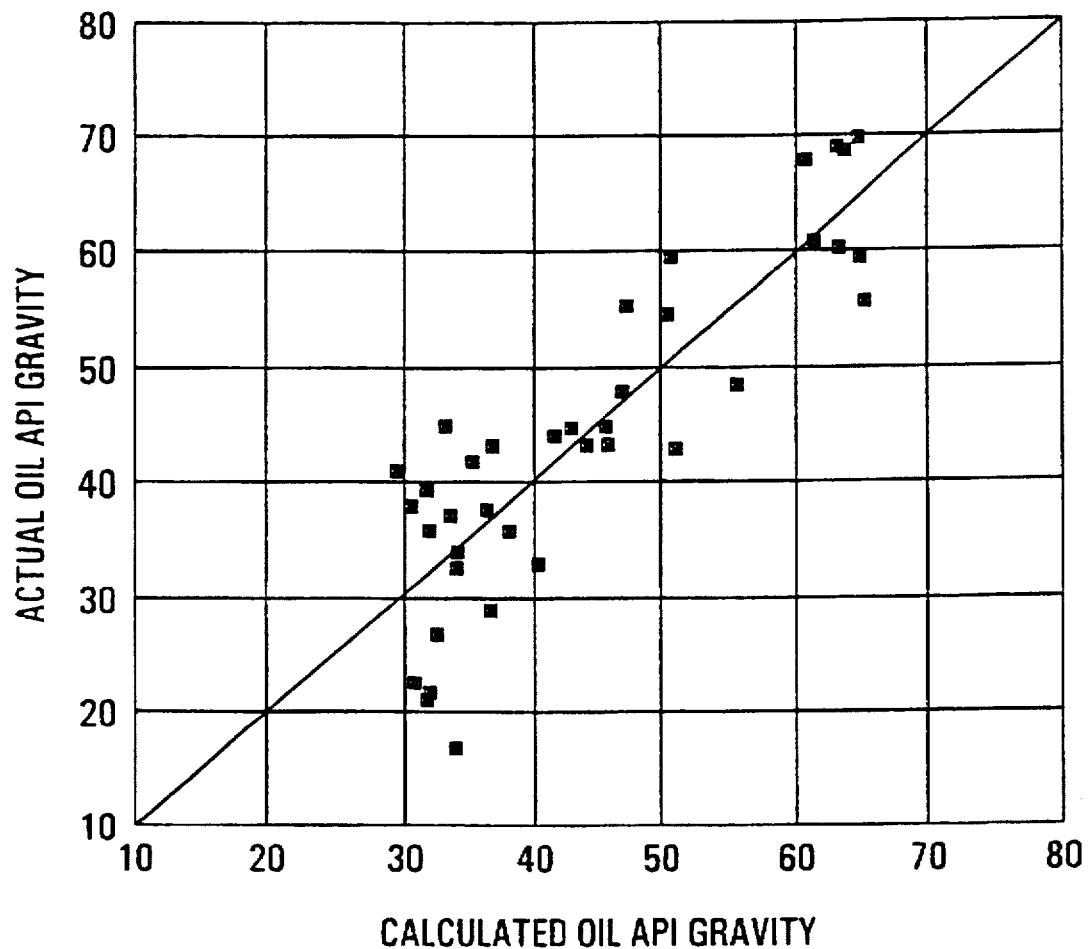
FIG. 4 is a plot of actual oil API gravity versus calculated oil API gravity, specifically showing actual oil API gravity using emission intensities at 290 and 365 nm (6.25% resolution) and 254 nm excitation.

FIG. 4 compares actual to predicted oil gravities. Again, while the estimated gravity is of limited accuracy, it is adequate in field situations to be of value in formation evaluation. Since gravity is a bulk property while fluorescence examines only the aromatic oil fraction, the lack of precise correlation is not surprising. Inclusion of additional intensity emission wavelengths to the regression in fact yields only a modest increase in predictive accuracy.

The numeric values for the equation coefficients given here are specific to the spectral response and calibration of the instrument used and are presented for illustrative purposes only. Emission spectra are artificially broadened to mimic use of 6.25% resolution filters rather than a precision grating monochromator.

The following examples will further illustrate the novel method of determining API gravity and wt. % from formation samples by the preferred embodiment and calculated using algorithms. These examples are given by way of illustration and not as limitations on the scope of the invention. Thus, it should be understood that the steps of the invention method may be varied to achieve similar results within the scope of the invention.

EXAMPLE 1

500 mg of cuttings were extracted with 5 ml. of heptane. Dilution by a factor of 1000 was required to bring the fluorescence to the linear response range. Measured intensity values in instrument units were:

EM1 (290 nm)=48.74 and EM2 (365 nm)=1867
Calculated values:

R=48.74/1867=0.0261 intensity ratio

Y=exp[0.9494+0.6575/(0.0261+0.11)]=324 units/(mg/l)

mg/l Oil (diluted)=0.5·(49+1867)/324=2.96 mg Oil in 5 ml Extract=1000 dil·2.96·0.005=14.8

Est Wt. % Oil in cuttings=100·(14.8/500)=3.0%

Est Gravity=66.05−3.170/(0.0261+0.06)=39 deg API

EXAMPLE 2

Sidewall core sample 500 mg of solids were extracted with 5 ml of heptane.

Dilution by a factor of 200 was required to bring the fluorescence to the linear response range. Measured intensity values in instrument units were:

EM1 (290 nm)=183.9 and EM2 (365nm)=1607
Calculated values:

R=183.9/1607=0.1144 intensity ratio

Y=exp [0.9494+0.6575/(0.1144+0.11)]=48.4 units/(mg/l)

mg/l Oil (diluted)=0.5·(184+1607)/48.4=18.5 mg Oil in 5 ml Extract=200 dil·18.5·0.005=18.5

Est Wt. % Oil in core=100·(18.5)/500)=3.7%

Est Gravity=66.05−3.170/(0.1144+0.06)=48 deg API

Est Oil Density=141.5/(131.5+48)=0.79 g/cc

Assuming a core bulk density of 2.5 g/cc, the volume % of oil is estimated to be 3.7·2.5/0.79=12%.

EXAMPLE 3

Environmental soil sample 500 mg of soil was extracted with 5 ml of heptane.

Dilution by a factor of 10 was required to bring the fluorescence to the linear response range. Measured intensity values in instrument units were:

EM1 (290 nm)=97.56 and EM2 (365 nm)=1888
Calculated values:

R=97.56/1888=0.0517 intensity ratio

Y=exp [0.9494+0.6575/(0.0517+0.11)]=150.8 units/(mg/l)

mg/l Oil (diluted)=0.5·(98+1888)/150.8=6.58 mg Oil in 5 ml Extract=10 dil·6.58·0.005=0.329

Est Wt. % Oil in soil=100·(0.329/500)=0.066%

Est Gravity=66.05−3.170/(0.0517+0.06)=38 deg API

We claim:

1. A method for evaluating in the field the API gravity at wt. % oil of a sample of an underground formation which comprises the steps of:

adding a known volume of an underground formation sample in a known volume of a solvent to form a solvated sample;

exciting said solvated sample by irradiating with a single fixed excitation wavelength of ultra violet radiation and quantitatively measuring with a changeable filter portable fluorometer the emission fluorescence of said solvated sample and measuring its emission intensities at two separate wavelengths;

characterizing the oil by the ratio of said two measured emission intensities;

determining a calculated concentration of sample in the underground formation;

applying regression analysis to a data base of concentration of formation oils to obtain an equation which results in a calculated value of API gravity of said sample; and determining from said calculated value of API gravity of said sample an estimate of API gravity and wt. % of in situ oil in the earth formation from which said sample is obtained.

2. The method of claim 1 wherein the underground formation sample is an oil sample.

3. The method of claim 2 wherein said oil sample oil is selected from wellhead oil and processed oil.

4. The method of claim 2 wherein the formation samples are solvated in a solvent which will solvate hydrocarbons.

5. The method of claim 1 wherein said samples is a drill cutting.

6. The method of claim 1 wherein said samples in a side wall core samples.

7. The method of claim 1 wherein the solvent is a normal alkane selected from the group consisting of hexane, heptane and pentane.

8. The method of claim 1 wherein the solvent is selected from the group consisting of methanol, ethanol, 2-propanol, 2-methyl-2-propanol, and combinations thereof.

9. The method of claim 1 wherein the emission fluorescence is measured at a fixed excitation wavelength and emission intensity measurements at two different points.

10. The method of claim 9 wherein the excitation wavelength is 254 nm.

11. The method of claim 1 wherein the emission fluorescence is measured between about 250 and about 400 nanometers.

12. The method of claim 11 wherein the emission fluorescence is measured at 290 nm and at 365 nm.

* * * * *